United States Patent [19]

Duffy et al.

[11] Patent Number: 5,187,845
[45] Date of Patent: Feb. 23, 1993

[54] METHOD FOR HEATING CRIMPED FIBERS AND PRODUCT THEREOF

[75] Inventors: Joseph J. Duffy, Newark; Jerry F. Potter, Seaford; Elwood A. Roth, Seaford; Kalika R. Samant, Seaford, all of Del.; Maurice C. Todd, Chadds Ford, Pa.

[73] Assignee: E. I. Du Pont de Nemours and Company, Wilmington, Del.

[21] Appl. No.: 682,331

[22] Filed: Apr. 11, 1991

Related U.S. Application Data

[63] Continuation-in-part of Ser. No. 532,847, Jun. 1, 1990, abandoned.

[51] Int. Cl.$^5$ .......................... D02G 1/12; D02G 1/00; D01G 37/00
[52] U.S. Cl. ........................ 28/267; 19/66.1; 28/263; 428/399
[58] Field of Search .................... 19/66.1; 28/267

[56] References Cited

U.S. PATENT DOCUMENTS

| Re. 23,824 | 5/1954 | Rainard | 19/66 |
|---|---|---|---|
| 2,575,781 | 11/1951 | Barach | 19/66 |
| 3,160,941 | 12/1964 | Williamson | 28/1 |
| 3,305,897 | 2/1967 | Meibohm | 19/66 |
| 3,859,695 | 1/1975 | Erickson | 28/17 |
| 3,911,539 | 10/1975 | Hughes et al. | 28/72.14 |
| 3,946,469 | 3/1976 | Benson | 28/72.14 |
| 3,965,548 | 6/1976 | James, II et al. | 28/17 |
| 3,975,807 | 8/1976 | Bramley et al. | 28/16 |
| 4,115,907 | 9/1978 | Lawson et al. | 28/266 |
| 4,221,838 | 9/1980 | Hughes et al. | 428/369 |
| 4,268,940 | 5/1981 | Kuroda et al. | 28/255 |
| 4,343,069 | 8/1982 | McLuskie et al. | 19/6 |

FOREIGN PATENT DOCUMENTS 1902960 1/1975 Fed. Rep. of Germany .

OTHER PUBLICATIONS

"Modified Stuffer Box Crimper", Product Licensing Index, Jun. 1970, p. 47.

Primary Examiner—George F. Lesmes
Assistant Examiner—Chris Raimund

[57] ABSTRACT

A method of producing crimped tow by continuously feeding a tow against an adjustable counter pressure means; the tow is maintained at an average predetermined thickness and steam enters the chamber and is exhausted from the chamber in a manner to provide uniform heating of the tow to provide a fiber that is uniformly annealed as determined by measuring light reflectance for yarn dyed with a structural sensitive Milling Blue "B" dye or shrinkage uniformity determined by thermal analysis.

2 Claims, 5 Drawing Sheets

METHOD FOR HEATING CRIMPED FIBERS AND PRODUCT THEREOF

RELATED U.S. APPLICATION

This application is a continuation-in-part of application Ser. No. 07/532,847 filed Jun. 1, 1990, now abandoned.

BACKGROUND OF THE INVENTION

This invention relates to an apparatus and method for uniformly heating synthetic polyamide fibers which are being crimped in a stuffer box crimper and, more particularly, it relates to uniformly heating crimped fibers in the stuffer box of the crimping apparatus and the resultant product. In the production of crimped fibers from drawn tow, it is known to form primary crimp between crimper feed rolls and an adjustable counter pressure means to regulate the discharge of the crimped fibers from an elongated crimping chamber. It is also known from U.S. Pat. Nos. 4,040,155 and 3,911,539 to Hughes and Erickson et al., respectively, to inject steam into the crimped fibers as they pass through the stuffer box and to provide a means for steam removal in the crimper chamber near its discharge as well as installation of pressure sensing taps within the crimper chamber for steam pressure control. As part of Hughes' and Erickson's disclosure, the presence of a broad range of pressure zones within the crimping chamber between the point of steam injection and steam removal is established. However, the uniformity of the annealed crimped product produced in this manner is somewhat less than satisfactory because of a number of factors such as poor penetration of steam into the dense folds of crimped fibers packed in the crimping chamber which results in uncontrolled or uneven heating of the crimped fiber as it passes through the stuffer box. Non-uniform heating or large pressure gradients in the stuffing box chamber results in fibers having variable dyeability and variable degrees of twist retention along their length which results in fuzzy uneven yarns that are unsuited for production of quality carpet products.

Conventional vented stuffing boxes as described by Hughes and Erickson are designed with a series of injection holes in the upper portions of the crimping chamber and generally a lesser number of holes in the lower chamber near the exit for venting. Measurement of flow from vent ports for such devices show that when steam or compressed air is injected into a location in the upper positions of the box, most of the flow short circuits down the side walls to the first vent location. Little cross flow occurs. Short circuiting of steam flow down the side walls of the chamber due to high product density or packing in the upper regions of the crimping chamber which prevent steam penetration into the bundle and causes the steam to flow along the path of least resistance, i.e. down the side walls of the stuffing box.

SUMMARY OF THE INVENTION

This invention employs a method for steam injection and venting which, when combined with careful selection of the denier loading (denier load per inch of crimper width), line speed, residence time, tow moisture levels, steam flow rate and pressure in the crimping chamber produces a product which is uniformly annealed along the entire length of the filament. More particularly, the method involves delivering an uncrimped drawn tow to a pair of crimper feed wheels with a precisely controlled cross section to maximize the crimp uniformity potential and heating the tow in the crimping chamber with steam at a pressure of less than 20 psig at a controlled rate of about 0.02 to about 0.10 pounds of steam per pound of tow. The tow has a moisture level of from about 4 to about 8 percent and a temperature of from about 100° C. to about 130° C.

The temperature of the tow being fed to the crimping chamber is maintained in the range of from about 65° C. to about 95° C.

DETAILED DESCRIPTION OF THE ILLUSTRATED EMBODIMENT

Figure 1:
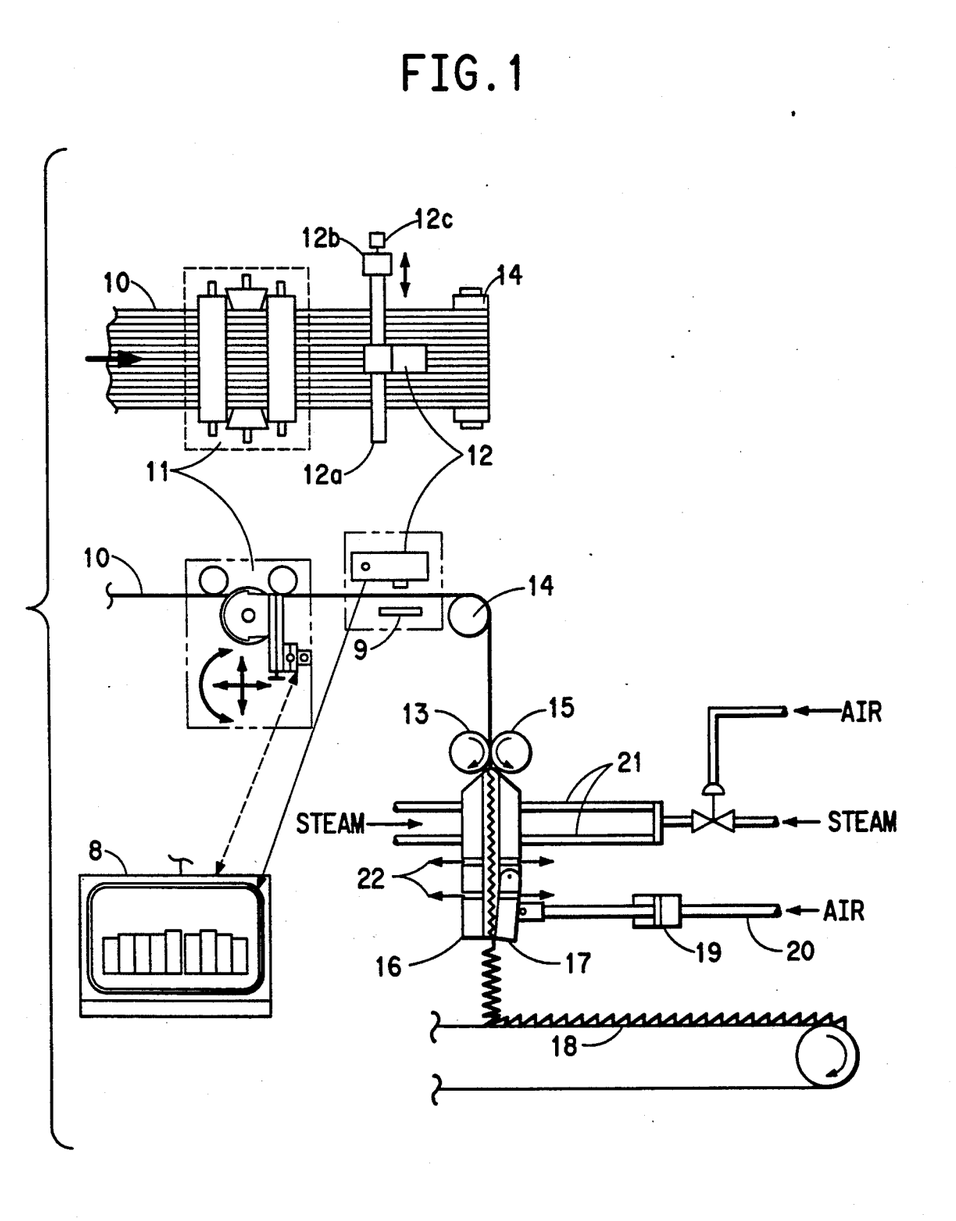
FIG. 1 is a schematic of a continuous process for crimping a drawn tow.

For an explanation of the process, attention is invited to FIG. 1 wherein a drawn yarn bundle or tow 10 of continuous synthetic filaments is fed from a draw machine (not shown) over a roll 14 into a stuffer box crimper chamber 16 by means of driven feed rolls 13 and 15. Prior to roll 14 the tow passes through a system which continuously monitors and controls the shape of the tow. The indexing sensor assembly 12 sends a signal to the monitor 8 which in turn provides a visual picture of the cross sectional shape of the tow. The cross section monitor 12 is moved across the running tow band 10 by a traverse screw 12a driven by a stepping motor 12b and its location is determined by a shaft encoding device 12c which sends a signal to a remote operator monitoring and control station 8. As the sensor 12 moves across the tow band 10 it measures the density of discrete sections 7 of the tow band (FIG. 4) normally in the range of 0.20 inches wide. A reflective tile 9 is provided to amplify the reflected signal from the infrared sensor 12 and to provide a constant thermal background. Scanning rates of the indexing system provided by Aldridge, Inc, Virginia Beach, VA are about 30-100 inches per minute. Scan rates and lane width can be altered to suit the process depending of the level of sensitivity and precision desired. By raising or lowering the sensor 12 or changing its indexing rate the sensitivity can be altered. Knowledge of actual band thickness is not necessary for process control only differences in band density. The discrete bands sensed by the moving sensor 12 are displayed on a remote operator display module 8 as a histogram. This information is used by the machine operator to position the remote motorized tow guide 11 to obtain the desired shape. This system allows the operator to insure a predetermined cross sectional shape is fed to the crimper and to detect a process upset which could affect crimp uniformity throughout a production run.

Tow 10 is directed into chamber 16 against the combined force of the mass of crimped tow held compacted in the chamber and the force applied by counter pressure means which may be a pivoted clapper 17 in the side wall of chamber 16 acted on by air cylinder 19 supplied with variable air pressure through pipe 20. Tow builds up in the crimper chamber 16 until the pressure in the chamber is sufficient to move clapper 17 when crimped tow is forced from the chamber onto a collecting belt 18 for transportation to the next steps in the process which may be a collection step followed by cutting the tow into staple lengths (not shown).

Figure 2:
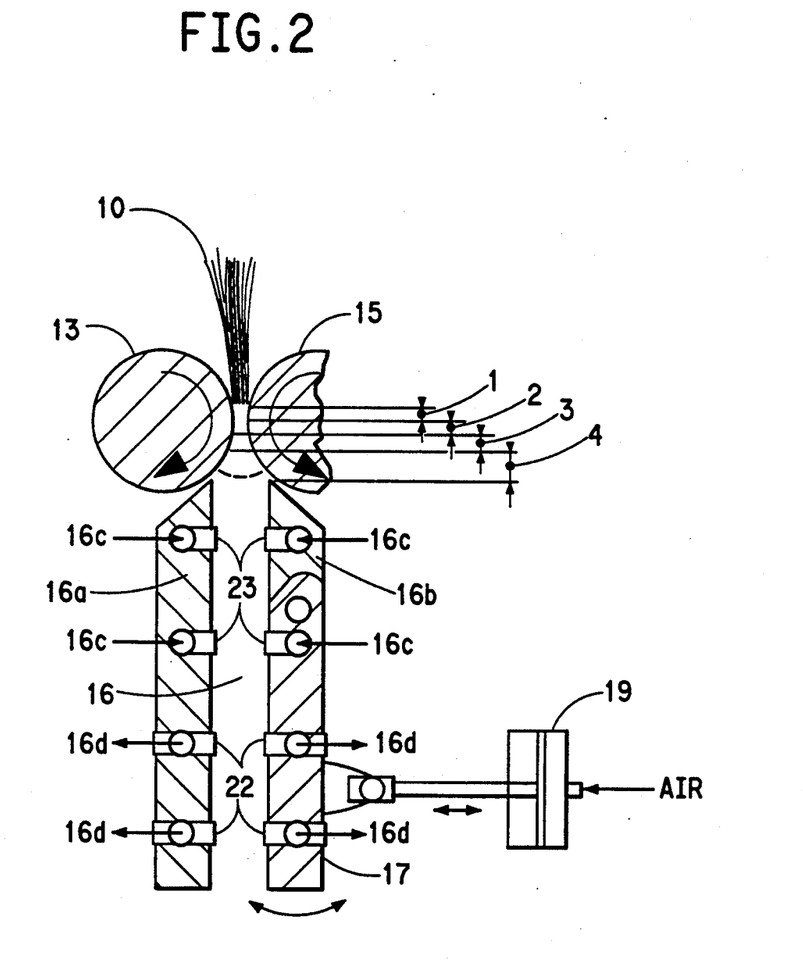
FIG. 2 is a cross-sectional elevation view of one embodiment of the stuffing box crimper.
Figure 3:
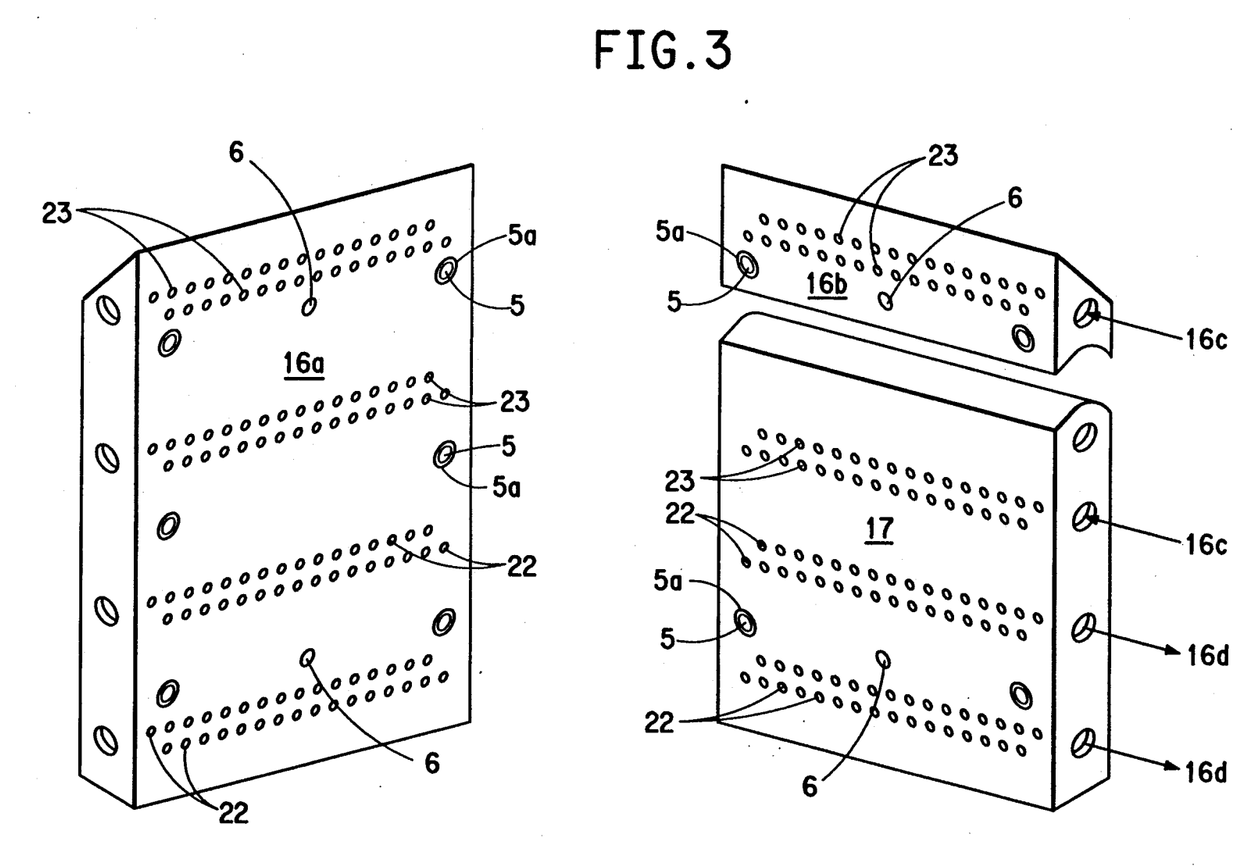
FIG. 3 illustrates the hole pattern used for steam injection and vent ports.

Referring to FIG. 2, the stuffing box crimper comprises two feed rolls 13, 15 which grip tow 10 and compress it in a first high compression zone 1 under heavy loading in the range of 3,000 to 5,000 psi on the feed wheels. In a second zone 2, primary bucking of the filaments occurs. In a third zone 3, a rotation occurs and individually crimped filaments and filament bundles are combined into thicker columns and then folded in zone 4 before passing into stuffer chamber 16. Chamber 16 comprises opposed walls 16a and 16b (which is partially defined by clapper 17). Two steam injection manifold passages 16c are located in each wall followed by two vent manifold passages 16d in each wall located below the injection manifolds 16c. Each injection manifold is connected to a series of holes 23 leading to chamber 16. The injection holes as shown in FIG. 3 are arranged across the width of the walls 16a, 16b and the gate 17 in two closely spaced rows to provide an essentially continuous flow of steam into the moving tow band. Exhaust steam is delivered from the tow to the vent manifold 16d through holes 22 also closed spaced across the width of walls 16a, 16b and the gate 17 and the vent holes are staggered in two closely spaced rows to provide an essentially continuous vent. By maintaining flow areas and velocities at minimum levels the pressure drop through the stuffing box from the point of injection to venting is maintained within 2 psig which results in stable low temperature annealing at high heat flux levels.

A series of insulated thermocouples 5 and pressure taps 6 are provided across and along the faces of the walls 16a, 16b and the face of gate 17 (FIG. 3) to monitor process parameters and to detect upsets such as a plugged vent port. The temperature sensors 5 are mounted in Vespel TM sleeves 5a to insulate them from the stuffing box chamber walls to provide precise readings of internal stuffing box steam or annealing fluid temperature. The outputs from the pressure taps and thermocouples are fed to a programmable logic controller, such as an Allen Bradley PLC-5, for routine process monitoring. A stand alone model 352 electronic controller manufactured by Moore Products, Springhouse, PA and a companion steam flow sensor are provided for steam flow control (Items not shown).

Figure 4:
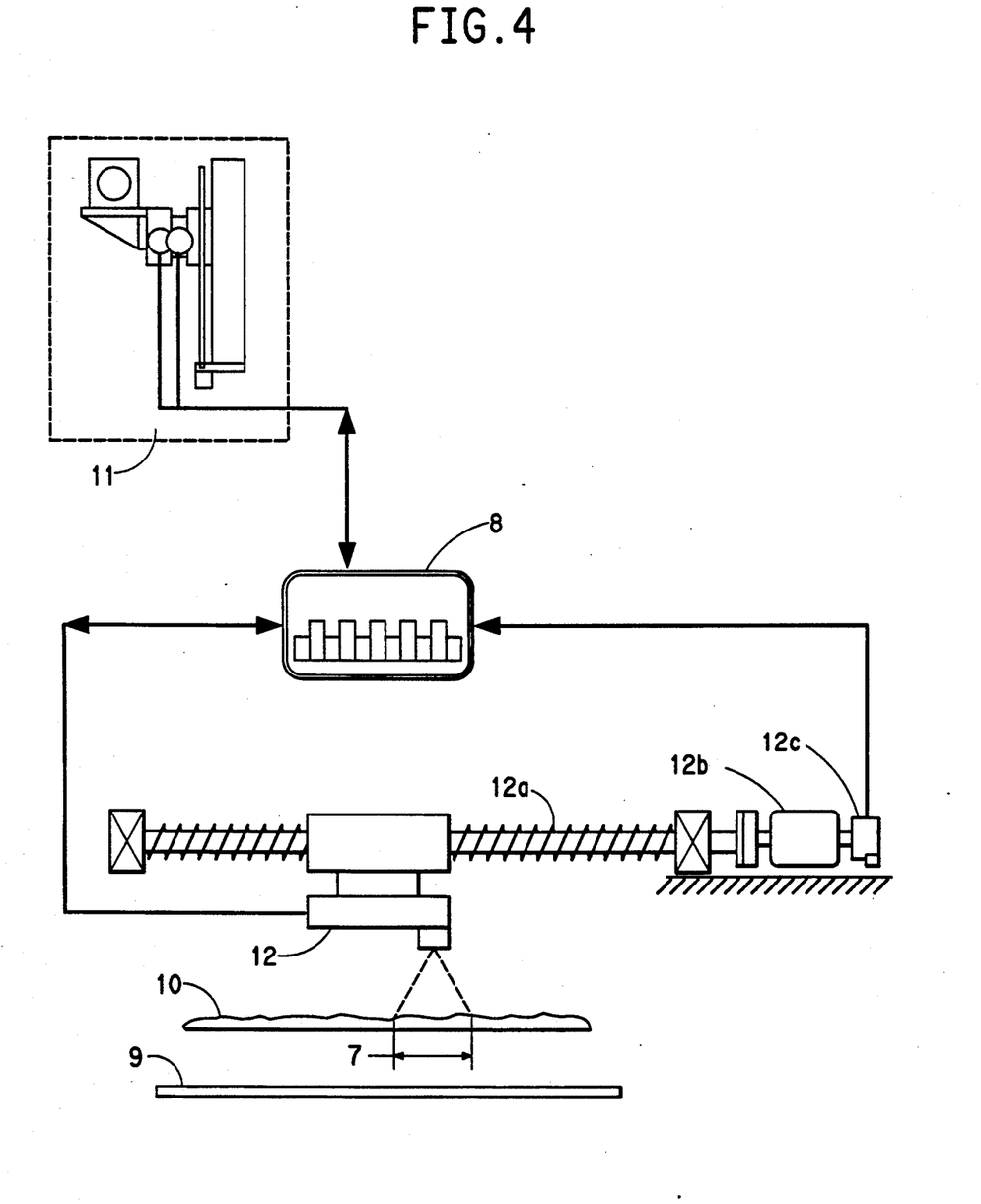
FIG. 4 is a schematic illustration of the adjustable guides used to establish the thickness and shape of the tow entering the crimper.

A preferred embodiment for accomplishing the task of monitoring and controlling the shape of the tow band entering the crimper is shown in FIG. 4 wherein a density gauge 12, such as a Microquad 8000 infrared sensor by Moisture Systems Corporation, Hopkinton, MA scans the tow band 10 and provides a visual picture of the tow band on a monitor 8. A machine operator upon viewing the tow band depicted on monitor 8 adjusts the guiding apparatus 11 to establish a uniform predetermined cross section.

Figure 5A:
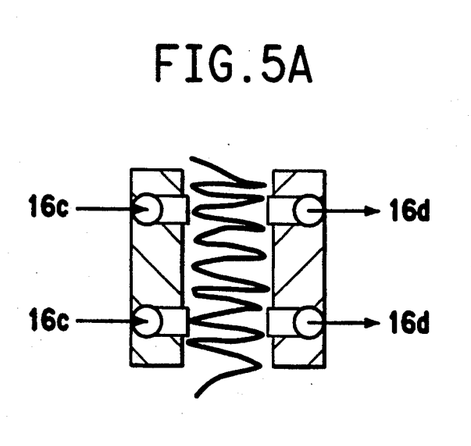
FIG. 5 is a schematic of alternate steam injection and venting profiles.
Figure 5B:
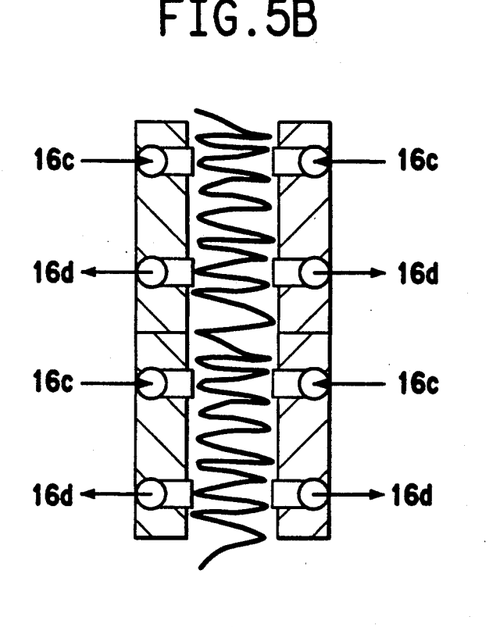
Figure 5C:
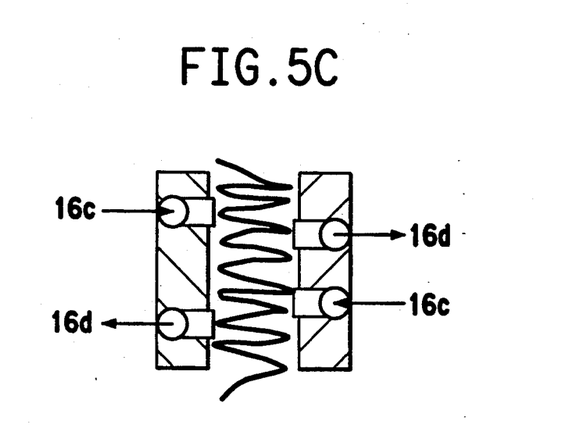

An alternate method FIG. 5 for steam injection and venting is preferred for very wet products. It consists of alternating injection and venting ports 16c and 16d to promote rapid heating and removal of excess condensate to improve heat transfer and penetration into the crimped tow band. In FIG. 5a steam is injected into port 16c and exists from ports 16d on the opposite side of the box. This configuration is useful only with very low density products and provides a flow through heating. In FIG. 5b steam is injected in port 16c and exhausted through port 16c in two or more steps on each face of the crimping chamber. This process has proven to be helpful at removing condensate build-up when very wet products are steam annealed. It allows for improved heating and greater heat transfer. In FIG. 5c steam is injected into port 16c and exhausted through ports 16d. The porting configuration is reversed with each cycle. It is a preferred method for cross flow heating and several cycles are recommended for complete heating.

As uncrimped tow, normally in the range of 50,000 to 400,000 denier per inch of roll width, enters the crimping chamber, the highly compressed bundle of fibers buckles imparting a permanent crimp to the filaments. A side plate or disc is provided to hold the bundle captive as it enters the crimper and is transferred to the stuffing box below the feed wheels. The crimping and packing process occurs in a series of discrete zones of activity.

In the first zone, the fiber tow bundle is compressed under heavy loading in the range of 3,000 to 5,000 psi by the action of the crimping feed wheels.

In a second zone primary buckling of the composite section of filaments occurs if the cross sectional uniformity of the tow bundle fed into the crimper is uniform across its width. For products at constant temperature and moisture, local variations in band uniformity cause changes in crimp frequency. Thin sections result in slightly lower frequency and heavy sections in slightly higher frequency crimp. If the variability is excessive local slippage occurs in the thin region and very low crimp is produced. This low crimp can cause operational and performance problems in subsequent processing and the final spun staple product. Guiding facilities are provided at the infeed to the crimper to insure a uniform cross section of fibers is fed to the crimper.

In a third zone a rotation occurs and individually crimped sections are combined into thicker secondary columns. As the void space between the rolls further diverges, the secondary column buckles forming large dense folds. The larger folds containing void areas, which allow steam penetration, move down the roll surfaces into the stuffing box. If denier loading in the stuffing box, the tow temperature and water content are carefully controlled, a steady and generally lower gate pressure is needed to impart the desired crimp level which reduces the packing density in the stuffing box which in-turn increases the porosity and steam penetration potential of the moving fiber wad.

As the highly compressed folded tow bundles enter the crimping chamber and pass the knife edges of the stuffing box walls, side wall pressure drops considerably. The rate of pressure reduction in the crimping chamber can be controlled by adjusting the box shape or geometry and denier loading. Because of the presence of steam in the crimping chamber a hydraulic distribution of load occurs and the density profile along the chamber walls can be assessed. This assessment has led to a relationship for crimper chamber geometry which is useful in establishing the pressure density profile and selection of optimum locations for injection and venting holes as well as limiting the pressure drop through the stuffing box. This relationship as follows shows an exponential loading down the the chamber and it has been used to establish optimum box shape for best crimp control and steam penetration as well as placement for injection and vent ports.

$$Inlet\ Force = Exit\ Force\cdot e^{\theta}[2*C*F*\{((A+B)*L)/(A*B)\}]$$

Where:
C=A constant ~0.3
F=Friction factor of yarn to metal
A=Box inlet width, B=Box inlet thickness
L=box length As the wad of compressed fibers moves down the stuffing box, its density decreases exponentially. As the density decreases, void areas open up allowing steam injected from both sides of the crimping chamber through a series of holes along the side walls to penetrate the tow. This apparatus improves on previous concepts by allowing the steam to be injected along several rows at different elevations in the chamber and to exit through another series of vent ports strategically placed along the chamber side walls to allow maximum exposure time and penetration into the crimped folds without overheating. The holes are sized and positioned to form a continuous flow across the face of the chamber to provide uniform heating and exposure to all segments of the tow. Typical spacings for injection and venting holes are 0.078" diameter holes spaced on 0.188" center lines in two adjacent rows spaced on 0.289" center lines. A preferred arrangement is to use two pairs of adjacent rows on both sides of the chamber for steam injection and an additional two pairs on both sides for venting. However, depending on the chamber shape, the pattern for injection and venting can be altered to promote cross flow by repeated injection and venting. Optimum injection and venting areas are established by monitoring inlet and exit flow rates, and steam temperatures and pressures within the crimping chamber under varying dynamic conditions. The best configuration for injection and venting also varies with the denier loading in the crimping chamber and chamber geometry (Box inlet thickness, width, length and internal angles (e.g. convergent to divergent cross section of the box in the operational position). Steam flowing through the holes is varied from 0.02 to 0.10 pounds of steam per pound of product for yarn at about 4 to about 8% nominal moisture level and stuffing box temperature is controlled within the range of from about 100° C. to about 130° C. to limit the amount of annealing. Steam flow rate control is preferred over pressure control as practiced by Hughes and Erickson. A flow control system ensures desired steam flow and heat input whereas a pressure control system can provide misleading control should the inlet ports be blocked. The large flow area, provided by the multiple injection rows of the present invention, ensures little pressure variation as the steam flow rate is varied to account for product density changes inside the stuffing box. By contrast, a pressure control system, such as used by Hughes and Erickson, can result in extremely low steam flow rates and heat input at low pressure levels. An increase in steam pressure, beyond the 10–14 psig, to achieve higher heat input will generally result in higher steam temperature and subsequently higher wall temperature causing non-uniform annealing. The use of pressure control as practiced by Hughes and Erickson results in varying heat levels as adjustments are made in crimper gate pressure in order to obtain different crimp levels or to compensate for other process variables. As tow water content increases to saturation, the steam flow rate must be increased to 0.2 to 0.3 pounds of steam per pound of product to provide adequate heating to achieve the desired level of annealing. Tows containing high moisture are more difficult to heat because condensation and surface water form a barrier which prevents steam penetration. In this type of operation, repetitive heating and venting cycles are required. Injection area and vent area need to be increased to maintain internal steam pressure and temperature within the desired process conditions of from about 100° C. to about 130° C. As steam flows through the tow, the act of condensation brings the entire bundle into equilibrium within 2–3 milliseconds because of the high heat transfer associated with two phase turbulent heat transfer in porous media. The use of slightly superheated steam is preferred since superheated steam more easily penetrates the tow bundles, and as it condenses, it instantly heats up the fiber without significantly raising the moisture content. Since further penetration is difficult because of the condensed water barrier, the inside must be heated by conduction and diffusion due to the wicking action of the water. Rapid venting allows some of the entrained steam and water to be vented so that subsequent injected steam can further penetrate the fiber bundle. Unless the water content of the fiber bundle is kept very low, the inside fibers cannot be heated above the saturation temperature corresponding to the internal steam pressure, so maintaining low pressures is essential to product uniformity. The fiber temperature should be controlled with the desired range of from about 100° C. to about 130° C. if an optimum bulk and heatsetability balance is to be maintained. Lower temperatures provide softer hand, lower bulk products. Box length and internal volume should be adjusted to obtain the desired residence time and pressure balance needed for uniform product and the desired level of annealing.

Idealized conditions for this process are to provide inlet tow temperatures to the crimper in the range of from about 65° to about 95° C. (by means of a steaming operation ahead of the stuffing box) and to keep the steam pressure in the stuffing box below 10–14 psig so that tow temperatures do not exceed the goal limits of 100° to 130° C. limits established for optimum uniformity. These conditions were established by autoclave setting of tows and subsequent processing to establish the best balance of annealing levels for mill processing and final spun yarn uniformity. When these limits are applied to the stuffing box process, the tow uniformity is improved as described in later sections and much of the sensitivity to process changes, such as speed, are reduced. The flow of steam to the stuffing box chamber is controlled and modulated as a function of line speed to maintain a constant energy balance around the process.

This method of control allows for higher steam flows at lower pressures which means more total energy for heating but a lower level of annealing which improves twist retention and reduces fuzzing and better CV's in carpet yarns. It also promotes a cross flow of steam through the folded crimped tow, thereby uniformly annealing all the product and improving product uniformity as determined by:

1. Differential light reflectance along the filament length for yarn dyed with a structural sensitive Milling Blue "B" dye.

2. Differential shrinkage as determined by thermal analysis.
3. Crimp uniformity as determined by stated methods.
4. Mill performance potential as determined by yarn CV's.

Test Methods

Confirmation of the product uniformity and potential can be made by analysis of properties along a fiber's length. Location of position within a stuffing box can be made in the cut fibers by dyeing the product using a structure sensitive MBB dye. Areas of high steam flow and heating which occur along the side walls of the stuffing box will appear dark and areas of low steam flow and reduced heating will appear light. These areas can be further characterized to assess crimp durability to processing, differential shrinkage along the length of a filament, and crimp properties which affect final value and uniformity. This is accomplished by removing adjacent filaments (before dyeing) from cut tufts or tows, and then noting the regions of interest (after dyeing) where visible differences exist. The undyed filaments from these regions are then subjected to a series of analyses such as:

Data Shrinkage—Thermal Analysis

Objective: Assess the uniformity of annealing in a stuffer box from steam or hot fluid injection processes by determining the range of temperatures to which the filaments in the process were exposed. The differential shrinkage between the fibers at the stuffing box wall and center of the stuffing box is reported as delta percent shrinkage between these locations.

Equipment: Du Pont model 2100 Thermal Analyzer and Du Pont model 2940 thermal mechanical analysis (TMA) for single filament analysis.

Procedure

Calibrate the temperature of the TMA at a ramp rate of 50° C. per minute.
Select samples for analysis from inspection of crimp form along cut samples or by dyeing of adjacent samples using a structure sensitive dye to locate samples from the edges and centers of stuffing box crimping processes.
Cut a 1 cm sample length from the desired location, generally center or middle of the stuffing box.
Place single filament sample in model 2940 head and apply a 1 gram load.
Heat sample from 35° C. to 300° C. at a rate of 50° C. per minute.
Read percent shrinkage or elongation at 225° C. and record.
(Note: 225° C. was selected because this is near the twist set temperature used in commercial twist set units such as the Suessen and the uniformity of shrinkage or elongation at this level translates to the along-end uniformity of spun yarn.)
Method Error: Standard method error on single filament analysis is estimated at +/−0.20% shrinkage.

Delta Reflectance

Objective: To rate the color uniformity of staple product dyed with a structural sensitive Milling Blue "B" dye to assess the uniformity of annealing during the crimping process. Measurements made on dyed tows between areas along the stuffing box wall and at the center of the tow as processed through the stuffing box and results are reported as the delta reflectance between these discrete regions.

Equipment

ACS Applied Color Systems Inc. Princeton, NJ, model CS-5 Chroma-Sensor Spectrophotometer.
Rotary lab dyer with automatic cycle controller

Dyeing Procedure

For tow samples, air splice ends together to retain across band fiber alignment and dye using adjusted bath concentrations as stated below.
Dye cycle
  Hold timer 85 minutes
  Temperature rise 1.5° C. per minute
  Final temperature 85° C.
  Dye liquor (1% NAOH-200 ml, 33% NaH2PO4-200 ml, 10% Merpol HCS-200 ml, 0.1% Milling Blue "B" dye -250 ml.
  Liquor ratio: 12.5 ml of dye solution per gram of fiber.
For cut samples taken from bales, remove cut tufts which are in bundles and tie at ends with wire to insure adjacent fibers which are process through the crimper together are dyed together.

Dye Uniformity Assessment

Read reflectance in light and dark areas along length of tow to assess uniformity of annealing process. The difference is called delta reflectance. If areas are too small to fit in sensing area, cut out sections and group on a sample card. Compare an average of five locations for both light and dark areas on each sample at 430 nanometers (nm) frequency.
Group sections of light and dark regions along cut filaments and record reflectance readings for composite sections. Report range of observations as above.

Tow Crimp Analysis

Objective: Establish the crimp level in a staple tow bundle as defined by its percent retraction after exposure to a load for a given period of time.

Equipment: A tow clamp mounted on a frame directly below a flanged roller mounted on a bearing to prevent drag. A meter stick attached to the frame extending downwardly from the clamp. A separate weight with hook attached. The weight is designed to provide about 0.016 gram per denier load on the tow.

Procedure: Place a knot in the end of a 2 meter long length of tow, place the weight hook through the knot and careful feed the tow over the roller above the meter stick. Lift the weight from a resting position about 2-3 inches to tension the tow and engage the clamp. Place a tape on the tow at the beginning of the meter stick. After exposing the sample to the load for 2 minutes slide the hook out of the tow and allow it to retract (relax) for an additional 3 minutes. Record the location of the tape on the meter stick after the 3 minute interval. The change from the stretched length to the relaxed or retracted length (in centimeters) is reported as tow crimp index or level.

Single Filament Crimp Analysis
Crimps Per Inch (CPI)

The Crimps Per Inch (CPI) is an indirect measure of yarn bulk. A filament is placed between two clamps and the original setting measured. Then a tension of 2 mg/denier is applied to the yarn and its relaxed length is measured. At this point a magnifying lamp is used to count the number of crimps between the clamps. Next, 50 mg/denier tension is applied and the extended length is recorded. This process is done one filament at a time and repeated until ten filaments have been measured. The results are averaged, and from the averaged results the CPI is calculated as follows:

$$CPI = \frac{\text{(number of crimps in filament)}}{\text{(length at 50 mg/denier } - \text{ original length)}} * 2.54 \frac{\text{inches}}{\text{filament}}$$

Filament Crimp Index (FCI)

The Filament Crimp Index (FCI) is calculated as follows:

$$FCI = \frac{\text{(length at 50 mg/denier } - \text{ length at 2 mg/denier)}}{\text{(length at 50 mg/denier } - \text{ original setting)}} * 100$$

FCI is really a measure of strain different stress levels; it is a measure of crimp take-up. FCI indicates the average per filament reduction in length caused by crimping. It does not, however, directly measure the number of crimps in a filament nor its amplitude.

EXAMPLES

The control examples, Items A and B, Table 1, illustrate product uniformity, mill performance and final carpet value for state of the art crimping equipment and procedures, i.e. without uniform tow band width control, without balanced denier loading and stuffing box geometry and without increased flow areas for steaming injection and venting at low and carefully controlled steam pressures and processing temperatures. The test items C, D and E, Table 2, were processed in accordance with procedures outlined above for this patent and illustrated in FIGS. 1-4.

Items A and B in Table 1 are illustrations of current practices for steam annealed stuffer box crimped products. Item A was produced using a conventional wet draw process and a 10 inch wide crimper manufactured by Fleissner GMBH and Co., Egelsbach, West Germany, and item B was produced using a crimper modified to duplicate the Hughes and Erickson unit. Both crimpers were operated to produce an essentially identical product as characterized by tow crimp measurements of percent retraction and single filament analysis of filament crimp index and crimp frequency, both commonly used methods to identify a product's crimp level and crimp form. Dye diffusion rates for both items A and B are high compared to the test items C-D in Table 2 at equivalent crimper speeds, which indicates a higher level of annealing and structural orientation for much of the fiber bundle. However, the uniformity of annealing as determined by differential reflectance and differential thermal analysis along the length of filaments showed considerable variability indicating a difference in the level of annealing between the edges and center of the folded tow in the stuffing box. The impact of this variable annealing upon final yarn quality is indicated by the singles yarn CV's shown.

Test items C-E were produced in accordance with the procedures and processes described herein. Injection area was increased 4.8X over that of the control units and the vent area increased 9.6X as shown in the Tables A-E. This change versus Items A and B resulted in lower dye diffusion rates at the same or higher steam flows and improved dye and structural uniformity as defined by differential reflectance and differential thermal analysis. The lower dye diffusion rate is due to lower operating temperatures in the stuffing box and lower levels of annealing.

The value of reduced moisture levels on overall uniformity as defined by delta reflectance and delta shrinkage as well as dye diffusion rate can also be seen by inspection of this data. The superior uniformity in product demonstrated in Examples C-E can only be achieved at lower steaming temperatures and complete heating throughout the fiber bundle in the stuffing box. This lower and more uniform orientation will allow for more complete twistsetting and more uniform final spun yarn as illustrated by comparison of CV's for control items A and B versus Examples C-E.

TABLE 1

| Process Parameter Item | Control A | Control B |
|---|---|---|
| Vent configuration | Unvented | Vented |
| Injection hole location | Top half box | Top half box |
| Vent hole location | None | Lower half box |
| Injection hole configuration | Multiple rows | Single row |
| Denier loading/inch box width | 200,000 | 270,000 |
| Moisture level in tow % | 14 | 7.4 |
| Steam flow lbs steam/lb fiber | 0.055 | 0.040 |
| Stuffer box injection pressure psig | 40 | 35 |
| Stuffing box steam temp. degrees C. | 146 | 141 |
| Crimper speed ypm | 220 | 630 |
| Tow Crimp level - % retraction (1) | 26.4 | 25.9 |
| Single filament crimp index (1) | 20.4 | 21.7 |
| Single filament crimp frequency (1) | 6.72 | 6.41 |
| Delta reflectance (1) | 17.80 | 12.64 |
| Delta shrinkage - thermal analysis (2) | 6.82 | 4.87 |
| Dye Diffusion rate sec -1 (2) | 227 | 162 |
| Single Yarn CV % (3) | 24.8 | 25.9 |

TABLE 2

| Process Parameter Item | Test C | Test D | Test E |
|---|---|---|---|
| Vent configuration | Vented | Vented | Vented |
| Vent hole location | Lower ¼ box | Lower ¼ box | Lower ¼ box |
| Injection hole location | Top/mid | Top/mid | Top/mid |
| Injection hole configuration | Multiple | Multiple | Multiple |
| Denier loading/inch box width | 270,000 | 200,000 | 200,000 |
| Moisture level in tow % | 7.2 | 7.2 | 7.4 |
| Steam flow lbs steam/lb fiber | 0.059 | 0.059 | 0.059 |
| Stuffer box injection pressure psig | 14 | 13 | 14 |
| Stuffing box steam temperature °C. | 126 | 125 | 126 |
| Crimper speed ypm | 630 | 630 | 200 |
| Tow Crimp level - % retraction (1) | 27.1 | 25.9 | 25.9 |
| Single filament crimp index (1) | 22.2 | 21.7 | 21.7 |
| Single filament crimp frequency (1) | 6.81 | 6.4 | 6.40 |
| Delta reflectance (1) | 4.66 | 4.45 | 4.02 |
| Delta shrinkage - Thermal analysis (1) | 0.155 | 0.150 | 0.142 |
| Dye Diffusion rate sec -1 (2) | 144 | 136 | 162 |
| Singles yarn CV % (3) | 23.3 | 23.2 | 21.0 |

(1) See Test Method section
(2) Du Pont dye diffusion rate procedure - (Investigating the Structure of Nylon Fibers by Measuring the Diffusion Coefficient of Acid Dyes. Part I: A semi-empirical, Approximate Solution to the Diffusion Equation" By H. Kobsa and C. M. Jones. Textile Research Institute Journal Number 55, (10) Pages 573 to 578 (1985)
(3) Uster Co. - Capacitive evenness tester - Singles yarn tested at 100 ypm speed for 12.5 minutes, average readings at 30 second intervals for 5 samples.

What is claimed is:

1. A method for producing crimped polyamide fiber tow comprising: continuously feeding tow from a draw machine against an adjustable counter pressure means in an elongated crimping chamber defined by opposed walls at a denier loading of from 200,000 to 270,000 per inch of crimping chamber width and discharging the tow, the improvement comprising: sensing and controlling the average predetermined thickness across the tow band as the tow advances to the crimping chamber; feeding the tow to the crimping chamber at a speed in the range of from 200 yards per minute to above 600 yards per minute at a temperature of from about 65° C. to about 95° C.; and heating the tow in the crimping chamber with steam at a pressure of less than 20 psig and at a controlled rate of 0.02 to about 0.10 pounds of steam per pound of tow, said tow having a 4 to 8 percent moisture level and a temperature of from about 100° C. to about 130° C., whereby the difference in percent shrinkage along the length of tow is less than about 0.2 percent as determined by thermal analysis and the reflectance difference along the length of the tow when dyed with a structural sensitive Milling Blue "B" dye is less than 5%.

2. The method of claim 1 wherein said crimped tow is then cut into staple length.

* * * * *